United States Patent
Logue et al.

(10) Patent No.: US 10,174,261 B2
(45) Date of Patent: *Jan. 8, 2019

(54) METHODS, SYSTEMS, AND APPARATUSES FOR UTILIZING A FISCHER-TROPSCH PURGE STREAM

(71) Applicant: SGCE LLC, Pasadena, TX (US)

(72) Inventors: Bruce Allen Logue, Sugar Land, TX (US); Scott Golczynski, Houston, TX (US)

(73) Assignee: SGCE LLC, Pasadena, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/315,129

(22) PCT Filed: May 29, 2015

(86) PCT No.: PCT/US2015/033235
§ 371 (c)(1),
(2) Date: Nov. 30, 2016

(87) PCT Pub. No.: WO2015/184292
PCT Pub. Date: Dec. 3, 2015

(65) Prior Publication Data
US 2017/0158965 A1    Jun. 8, 2017

Related U.S. Application Data

(60) Provisional application No. 62/005,118, filed on May 30, 2014.

(51) Int. Cl.
*C10G 2/00* (2006.01)
*C10L 3/10* (2006.01)
(Continued)

(52) U.S. Cl.
CPC ............ *C10G 2/40* (2013.01); *C01B 3/16* (2013.01); *C01B 3/32* (2013.01); *C07C 1/10* (2013.01);
(Continued)

(58) Field of Classification Search
CPC . C01B 3/382; C01B 3/384; C01B 2203/0233; C01B 2203/0244;
(Continued)

(56) References Cited

U.S. PATENT DOCUMENTS

2007/0010590 A1* 1/2007 Abbott ............... B01J 8/025
518/703
2014/0357737 A1* 12/2014 Abbott ............... C10K 1/005
518/704

FOREIGN PATENT DOCUMENTS

WO    2011048066    4/2011

OTHER PUBLICATIONS

Linde AG, Engineering Division, https://www.linde-engineering.com/en/process_plants/hydrogen_and_synthesis_gas_plants; 3 pages, Apr. 23, 2018.
(Continued)

*Primary Examiner* — Jafar F Parsa
(74) *Attorney, Agent, or Firm* — Timothy S. Westby; Porter Hedges LLP

(57) ABSTRACT

Systems, apparatuses and methods of utilizing a Fischer-Tropsch ("FT") tail gas purge stream for recycling are disclosed. One or more methods include removing an FT tail gas purge stream from an FT tail gas produced by an FT reactor, treating the FT tail gas purge stream with steam in a water gas shift ("WGS") reactor, having a WGS catalyst, to produce a shifted FT purge stream including carbon dioxide and hydrogen, and removing at least a portion of the carbon dioxide from the shifted FT purge stream, producing
(Continued)

a carbon dioxide stream and a treated purge stream. Other embodiments are also disclosed.

22 Claims, 5 Drawing Sheets

(51) Int. Cl.
    *C10K 1/00*     (2006.01)
    *C07C 1/10*     (2006.01)
    *C10J 3/00*     (2006.01)
    *C10K 3/04*     (2006.01)
    *C10G 49/00*     (2006.01)
    *C10K 1/14*     (2006.01)
    *C01B 3/16*     (2006.01)
    *C01B 3/32*     (2006.01)

(52) U.S. Cl.
    CPC ............. *C10G 2/00* (2013.01); *C10G 49/007* (2013.01); *C10J 3/00* (2013.01); *C10K 1/00* (2013.01); *C10K 1/005* (2013.01); *C10K 1/143* (2013.01); *C10K 3/04* (2013.01); *C10L 3/10* (2013.01); *C01B 2203/0205* (2013.01); *C01B 2203/0283* (2013.01); *C01B 2203/0475* (2013.01); *C01B 2203/062* (2013.01); *C01B 2203/1241* (2013.01); *C01B 2203/148* (2013.01); *C10G 2300/1022* (2013.01); *C10G 2300/42* (2013.01)

(58) Field of Classification Search
    CPC ...... C01B 2203/0405; C01B 2203/042; C01B 2203/062; C01B 2203/0844; C01B 2203/1241; C01B 2203/141; C01B 2203/143; C01B 2203/82; C10G 2/32; C10G 35/04; C10G 9/36; C10G 70/00; C10G 2300/807
    See application file for complete search history.

(56) References Cited

OTHER PUBLICATIONS

Office Action dated Jan. 24, 2018 for Canadian Patent Application No. 2,950.291, 4 pages.

\* cited by examiner

METHODS, SYSTEMS, AND APPARATUSES FOR UTILIZING A FISCHER-TROPSCH PURGE STREAM

RELATED APPLICATIONS

This application claims priority to U.S. Provisional Patent Application No. 62/005,118, entitled "Methods, Systems, and Apparatuses for Utilizing a Fischer Tropsch Purge Stream," filed May 30, 2014, having assignee patent file number GI-0037-US-P01, incorporated in its entirety by reference. This application is also related to U.S. Provisional Application No. 62/005,102, entitled "Methods, Systems, and Apparatuses for Recycling Fischer-Tropsch Water and Fischer-Tropsch Tail Gas" and having assignee patent file number GI-0032-US-P01, incorporated in its entirety by reference.

BACKGROUND

Field of the Invention

The present invention relates to a systems, methods, and apparatuses for Fischer-Tropsch liquid hydrocarbon production. Specifically, the present invention relates to a system and method for utilizing a Fischer-Tropsch purge stream.

Background of the Invention

The Fischer-Tropsch (or "Fischer Tropsch," "F-T" or "FT") process (or synthesis or conversion) involves a set of chemical reactions that convert a mixture of carbon monoxide and hydrogen (known as reformed gas, synthesis gas, or "syngas") into liquid hydrocarbons (called "liquid FT hydrocarbons" herein). The FT liquid hydrocarbons may include a wax ("FT wax") that may be liquid when produced but becomes solid as it cools. The process was first developed by German chemists Franz Fischer and Hans Tropsch in the 1920's. The FT conversion is a catalytic and exothermic process. The FT process is utilized to produce petroleum substitutes, typically from carbon-containing energy sources such as coal, natural gas, biomass, or carbonaceous waste streams (such as municipal solid waste), the petroleum substitutes being suitable for use as synthetic fuels, waxes and/or lubrication oils. The carbon-containing energy source is first converted into a reformed gas, using a syngas preparation unit in a syngas conversion. Depending on the physical form of the carbon-containing energy source, syngas preparation may involve technologies such as steam methane reforming, gasification, carbon monoxide shift conversion, acid gas removal, gas cleaning and conditioning. These steps convert the carbon source to simple molecules, predominantly carbon monoxide and hydrogen, which are active ingredients of synthesis gas. Syngas also contains carbon dioxide, water vapor, methane, and nitrogen. Impurities deleterious to catalyst operation such as sulfur and nitrogen compounds are often present in trace amounts and are removed to very low concentrations as part of synthesis gas conditioning.

Once the syngas is created and conditioned, the conditioned syngas is used as an input to an FT reactor (also called an "FT synthesis reactor") having an FT catalyst to make the liquid FT hydrocarbons in a Fischer-Tropsch synthesis process. Depending on the type of FT reactor that is used, the FT conversion of the syngas to liquid FT hydrocarbons takes place under appropriate operating conditions.

Turning first to the syngas conversion step, to create the syngas from a natural gas feedstock, for example, methane in the natural gas reacts with steam and/or oxygen in a syngas preparation unit to create syngas. Some syngas preparation units include a syngas catalyst (also called a reformer catalyst), while others do not. The syngas comprises principally carbon monoxide, hydrogen, carbon dioxide, water vapor and unconverted methane. When partial oxidation is used to produce the synthesis gas, the syngas typically contains more carbon monoxide and less hydrogen than is optimal and consequently, the steam is added to the react with some of the carbon monoxide in a water-gas shift reaction. The water gas shift reaction can be described as:

$$CO + H_2O \rightleftharpoons H_2 + CO_2 \qquad (1)$$

Thermodynamically, there is an equilibrium between the forward and the backward reactions. That equilibrium is determined by the concentration of the gases present.

The Fischer-Tropsch (FT) reactions for the FT conversion of the syngas to the liquid FT hydrocarbons may be simplistically expressed as:

$$(2n+1)H_2 + nCO \rightarrow C_nH_{2n+2} + nH_2O, \qquad (2)$$

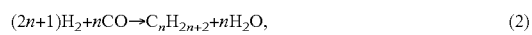

where 'n' is a positive integer.

Turning now to the FT conversion step, the FT synthesis reaction is performed upon the conditioned syngas in the presence of a catalyst, called a Fischer-Tropsch catalyst (or "FT catalyst"). Unlike a reagent, a catalyst does not participate in the chemical reaction and is not consumed by the reaction itself. In addition, a catalyst may participate in multiple chemical transformations. Catalytic reactions have a lower rate-limiting free energy of activation than the corresponding un-catalyzed reaction, resulting in higher reaction rate at the same temperature. However, the mechanistic explanation of catalysis is complex. Catalysts may affect the reaction environment favorably, or bind to the reagents to polarize bonds, e.g. acid catalysts for reactions of carbonyl compounds, or form specific intermediates that are not produced naturally, such as osmate esters in osmium tetroxide-catalyzed dihydroxylation of alkenes, or cause lysis of reagents to reactive forms, such as atomic hydrogen in catalytic hydrogenation.

In addition to liquid hydrocarbons, Fischer-Tropsch synthesis also commonly produces gases ("Fischer-Tropsch tail gases" or "FT tail gases") and water ("Fischer-Tropsch water" or "FT water"). The FT tail gases typically contain CO (carbon monoxide), $CO_2$ (carbon dioxide, which may also be written informally as "CO2"), $H_2$ (hydrogen), light hydrocarbon molecules, both saturated and unsaturated, typically ranging from $C_1$ to $C_4$, and a small amount of light oxygenated hydrocarbon molecules such as methanol. Typically, the FT tail gases are mixed in a facility's fuel gas system for use as fuel.

The FT water may contain contaminants, such as dissolved hydrocarbons, oxygenates (alcohols, ketones, aldehydes and carboxylic acids) and other organic FT products. Typically, the FT water is treated in various ways to remove the contaminants and is properly disposed of.

FIG. 1 and FIG. 2 depict conventional systems. FIG. 1 depicts a simplified block diagram for a conventional Fischer Tropsch system, including a steam methane configuration. Natural gas 102 and steam 104 enter a syngas preparation unit 130, which, in the example of FIG. 1 comprises a steam methane reformer ("SMR"). Alternate conventional syngas preparation units may include a partial oxidation reformer, an autothermal reformer or a hybrid reformer, a partial oxidation reformer. Flue gas 132 and reformed gas ("syngas") 134 exit the SMR 130 via first and second flowlines respectively. (Flowlines in FIG. 1 are not numbered separately from the fluids therein)

Continuing to refer to FIG. 1, the reformed gas 134 typically includes hydrogen, carbon monoxide, carbon dioxide and methane. The reformed gas 134 passes to a syngas conditioning unit 160, whereby the gas is cooled, a process condensate stream 162 is recovered, and the hydrogen and carbon monoxide ratios of the reformed gas 134 are adjusted if necessary. Conditioned reformed gas 165 is sent via a third flowline to an FT synthesis reactor 170. Outputs for the FT reactor 170 include FT tail gas 172 that may be sent to a fuel system (not depicted), FT water 174 that may be sent to a treatment system (not depicted), and FT liquid hydrocarbons 180.

FIG. 2 depicts a more detailed view of the conventional SMR 130 of FIG. 1. A fuel gas flowline 206 conveying a fuel gas passes through a first flow control regulator 208 and to first and second burners 209a, 209b. A first combustion air flowline 211 carries combustion air to a forced draft fan 212. A second combustion air flowline 213 conveys the combustion air from the forced draft fan 212 to a combustion air heater 214, which heats the combustion air. The heated combustion air passes via a third combustion air flowline 215 to first and second burners 209a, 209b, where it is mixed and combusted with the fuel gas.

Continuing to refer to FIG. 2, a first natural gas feed flowline 202 conveys natural gas to a natural gas preheater 241, which heats the natural gas. The preheated natural gas feed is conveyed through a second natural gas feed flowline 227 to a mixed feed preheater coil 228, downstream of an intersection with a second flow control regulator 226, which injects steam into the natural gas feed to form a mixed gas feed. After the mixed gas feed is heated in the mixed feed preheater coil 228, a mixed feed gas flowline 229 conveys the heated mixed gas feed from the mixed feed preheater coil 228 to an input (not separately depicted) of an SMR tube 210 containing a steam methane reformer catalyst (not separately depicted). Various appropriate steam methane reformer catalysts are commercially available, including but not limited to those provided by Clariant and Johnson-Mathey. Exposed to higher temperatures from the first and second burners 209a, 209b and to the steam methane reformer catalyst, the feed gas becomes a reformed gas. A reformed gas flowline 231 conveys the reformed gas from an output (not separately depicted) of the SMR tube 210 to a reformed gas boiler 239.

Referring again to FIG. 2, a boiler feed water line 201 conveys a boiler water stream to a steam drum 216. A first water line 235 conveys water from the steam drum 216 to the reformed gas boiler 239. A steam-water mixture returns from the reformed gas boiler 239 to the steam drum 216 via natural circulation through a mixture flowline 236. A second water line 217 conveys water from the steam drum 216 to a steam generator 218 that generates steam from the water. A first steam line 219 conveys the steam from the steam generator 218 to the steam drum 216. Steam leaves the steam drum 216 via a second steam line 220a. Part of the steam in the second steam line 220a may be diverted through a third steam line 221 connected to the second steam line 220a. (Downstream of this connection, the second steam line is numbered 220b.) The third steam line 221 may convey steam to a turbine or to other parts of the plant. The second steam line 220b carries remaining steam, which was not diverted to the third steam line 221, to a steam superheater 223. The steam superheater 223 superheats the remaining steam to very high temperatures. For example, if the steam leaving the steam drum 216 in the second steam line 220a was at a temperature of about 450° F., then the steam superheater 223 may typically heat the remaining steam to a temperature of about 700° F. Superheated steam leaves the steam superheater 223 via a fourth steam line 224. The fourth steam line 224 is connected to a fifth steam flowline 261. The second flow control regulator 226 is positioned on the fifth steam flowline 261 downstream of its connection with the fourth steam line 224. Downstream of its connection with the fifth steam flowline 261, the fourth steam line 224 is connected to a third flow control regulator 225. The fifth steam flowline 261 feeds a portion of the superheated steam from the fourth steam line 224 into the second natural gas flowline 227 to be mixed with the natural gas in the second natural gas flowline 227, upstream of the mixed feed preheater coil 228. The second and third flow control regulators 226, 225 may be adjusted to allow a predetermined amount of the superheated steam into the second natural gas flowline 227. Thus, a mixture of steam and natural gas are conveyed as a feed gas in the mixed feed gas flowline 229 from the mixed feed preheater coil 228 to the input of the SMR tube 210.

Referring again to FIG. 2, when the reformed gas in the reformed gas flowline 231 has exited the SMR tube 210, the reformed gas may be at very high temperatures. A reformed gas temperature of about 1600° F. might be typical. The reformed gas flowline 231 conveys the reformed gas to the reformed gas boiler 239, which can cool the reformed gas to a first lower temperature, as an example, down to 800° F. Such a temperature may still be considered hot. A second reformed gas flowline 240 conveys the reformed gas from the reformed gas boiler 239 to the natural gas preheater 241, where the first lower temperature of the reformed gas is used to heat the natural gas feed from the first natural gas flowline 202. The reformed gas then passes through a third reformed gas flowline 234 to optional further cooling and/or treatment and to the FT reactor (not depicted in FIG. 2). Flue gas exits the SMR via a flue gas flowline 232, which carries the flue gas to an induced draft fan 233 and from the induced draft fan 233 to a flue gas stack 237.

In the conventional SMR 130 of FIGS. 1 and 2, FT tail gases may be mixed in a facility's fuel gas system for use as fuel. The FT water may contain contaminants, such as dissolved hydrocarbons, oxygenates (alcohols, ketones, aldehydes and carboxylic acids) and other organic FT products. Typically, FT water is treated in various ways to remove the contaminants and is properly disposed of.

U.S. Pat. No. 7,323,497 B2 by Abbott et al. ("Abbott"), incorporated in its entirety herein by reference for all purposes not contrary to this disclosure, describes an alternative to the conventional process described above with respect to FIGS. 1 and 2. Abbott includes the step of feeding "co-produced water" [FT water] "to a saturator wherein it is contacted with hydrocarbon feedstock to provide at least part of the mixture of hydrocarbon feedstock and steam subjected to steam reforming." (Abstract. See also Col. 10, lines 14-17.) However, while saturators are efficient, they may be expensive. In addition, saturators generally require a blow-down, the results of which must be properly disposed of. Moreover, using a saturator, the heated FT water in the saturator has a long residence time, which may result in unwanted side reactions among impurities producing heavy by-products. Abbott also discloses at least a two-stage reforming process. In the first stage, a partially reformed gas is produced through steam reforming. The steam reforming is performed after saturation of the feedstock with steam, the water for which may include FT water from the saturator. See Abbott, Column 4, lines 20-37. The steam reforming step may include "one or more (preferably one or two) stages of pre-reforming and/or primary steam reforming, to form a partially reformed gas." (Abbott, Column 4, lines 45-49.) In a second stage, the partially reformed gas:

is then subjected to a step of partial combustion. The partially reformed gas fed to the partial combustion vessel may preferably additionally comprise a tail gas from the Fischer-Tropsch synthesis and/or, carbon dioxide recovered from the synthesis gas. Where primary and secondary reforming are used to produce the reformed gas stream it may also be desirable, in order to reduce the reforming duty on the primary reformer, to bypass a portion of the hydrocarbon (or hydrocarbon/steam mixture) around the primary reformer and feed it directly to the secondary reformer. In forming the feed stream for the partial combustion stage, the Fischer-Tropsch tail gas, and/or carbon dioxide and/or second hydrocarbon stream, may be combined separately in any order to the partially reformed gas or may be pre-mixed if desired before being fed to the partially reformed gas.

(Abbott, Column 5, lines 19-34.) The partial combustion stage includes "combustion with a gas containing free oxygen supplied via burner apparatus." Abbott, Column 5, lines 50-53.) After combustion, "the hot partially combusted gas then passes through a bed of steam reforming catalyst to form the reformed gas mixture." Abbott, Column 6, lines 25-27.) Thus, in Abbott, the FT tail gas (and/or carbon dioxide and/or a second hydrocarbon) "is added to the partially reformed gas before partial combustion thereof." Abbott, Claim 7. In addition, Abbott indicates to avoid the undesirable build up of inerts, it is desirable only to utilize tail gas recycle when the partial combustion step is performed using substantially pure oxygen." (Abbott, Column 8, lines 27-30.) Sometimes, pure oxygen, as in the desirable embodiments disclosed by Abbott, is not readily available or is expensive to obtain. In addition, a single stage reformer might be preferred for some applications.

Abbott further discloses, "Typically the de-watered synthesis gas contains 5 to 15% by volume of carbon dioxide (on a dry basis). In one embodiment of the invention, after separation of the condensed water, carbon dioxide may be separated from the de-watered synthesis gas prior to the Fischer-Tropsch synthesis stage and recycled to the synthesis gas production. Such recycle of carbon dioxide is preferred as it provides a means to control H2/CO ratio to achieve the optimal figure for FT synthesis of about 2." (Abbott at Column 7, lines 5-13.)

U.S. Pat. No. 8,168,684 to Hildebrandt, et al. ("Hildebrandt"), incorporated in its entirety herein by reference for all purposes not contrary to this disclosure, discloses a Fischer Tropsch process with "$CO_2$ rich syngas." Hildebrandt defines a "$CO_2$ rich syngas" as "a gas mixture in which there is $CO_2$, $H_2$ and CO. The $CO_2$ composition in this mixture is in excess of the $CO_2$ which would usually occur in conventional syngas." (Hildebrandt at Column 2, lines 17-20.) The example described therein used coal as a feedstock. (See Hildebrandt at Column 4, line 32: "The feed considered was coal.") Hildebrandt also mentions the use of feedstocks comprising methane from natural gas (Hildebrandt at Column 3, lines 36-40 and Column 5, lines 23-25) and gas "generated by fermentation of natural waste dumps" (Hildebrandt at Column 5, lines 23-25). Hildebrandt at Column 2, lines 20-21 states: "The $CO_2$ is utilized as a reactant and is converted into the desired product." Claim 1 of Hildebrandt recites in part the production of "hydrocarbons according to the overall process mass balance:

$$CO_2 + 3H_2 \Rightarrow CH_2 + 2H_2O,"$$  (3)

which is an equation known to work with iron-based FT catalysts, but not known to work with cobalt-based FT catalysts. See, for example, "Comparative study of Fischer-Tropsch synthesis with $H_2$/CO and $H_2$/$CO_2$ syngas using Fe- and Co-based catalysts," T. Riedel, M. Claeys, H. Schulz, G. Schaub, S. Nam, K. Jun, M. Choi, G. Kishan, K. Lee, in APPLIED CATALYSTS A: GENERAL 186 (1999), pp. 201-213 ("Riedel et al."), which at page 212 concluded, "Fischer-Tropsch $CO_2$ hydrogenation would be possible even in a commercial process with iron, however, not with cobalt catalysts." Hildebrandt does not, however, disclose the FT catalyst or the type of FT catalyst used in the FT process(es) described therein.

Hildebrandt further notes, "Unreacted carbon dioxide, carbon monoxide and hydrogen may be recirculated from the Fischer Tropsch synthesis section (5) into the gasifier/reforming process stage (3) via a conduit (7) or back to the Fischer Tropsch synthesis section." (Hildebrandt at Column 3, lines 28-31.)

U.S. Pat. No. 6,632,846 B2 by Sheppard et al. (the "'846 patent"), incorporated herein in its entirety by reference for all purposes not contrary to this disclosure, also describes an alternative to the conventional process described above with respect to FIGS. 1 and 2 of the present disclosure. The '846 patent describes a "plant for manufacturing urea from carbonaceous materials, oxygen from an air separation unit and water, preferably steam, is made up of a syngas generator unit, an air separation unit, Fischer-Tropsch unit, a $CO_2$ removal unit, a hydrogen removal unit, a methanator unit, an ammonia converter unit and a urea synthesizer unit." ('846 patent, Abstract.) The '846 patent further discloses that "[e]ach of Fischer-Tropsch liquids, ammonia, hydrogen and urea can be recoverable under proper economic conditions. Electrical power is recoverable by the addition of at least one of a steam turbine and a gas turbine which is/are coupled to an electrical generator." ('846 patent, Abstract.) The '846 patent states, "Ammonia, carbon dioxide, hydrocarbons, electric power and urea are producible as products by the reaction of oxygen, water and a carbon source in a syngas generator to produce a syngas, utilizing a water gas shift mechanism to provide $CO_2$, reacting the syngas in an FT reactor to produce FT hydrocarbons and hydrogen, reacting the hydrogen with nitrogen from the air separation oxygen plant to form ammonia, then reacting the $CO_2$ and ammonia to form urea." ('846 patent, Col. 2, lines 24-31.) With respect to its own FIG. 1, the '846 patent states that treated syngas is "piped to the FT reactor and product separation unit 21 to obtain the liquid FT hydrocarbon products. The FT reactor and product separator 21 tail gas is piped to remove carbon dioxide via $CO_2$ removal unit 22. A second portion of the desulfurized syngas is piped to a water gas shift reactor 23, preferably designed for use with a high temperature iron/chrome catalyst. The tail gas stream from the FT reactor and product separation unit 21 is combined with the output of the shift reactor 23 [i.e. the shifted syngas] and passed through $CO_2$ removal unit(s) 22. Combustible components from the $CO_2$ removal unit(s) 22 are fed to the gas turbine 24 which is used to drive a coupled electricity generator 25." ('846 patent, Col. 3, lines 20-31.) In FIG. 2a of the '846 patent, "the non-$CO_2$ output of the $CO_2$ removal unit 22 is passed through a hydrogen ($H_2$) removal unit 28 and the recovered hydrogen is piped to an ammonia converter 38 (FIG. 2b). The hydrogen contains trace amounts of carbon monoxide which fuel the smaller methanator 34 (FIG. 3b). The non-$H_2$ output of the H2 removal unit (HRU) 28 is piped to the gas turbine 24 as fuel." ('846 patent, Col. 3, lines 41-47.) In FIG. 3A of the '846 patent, syngas is treated to remove CO$_2$ and then the treated syngas sent to an FT reactor. ('846 patent, Col. 4, lines 15-25.) In FIG. 3B of the '846 patent, "the FT tail gas stream then passes a pressure swing absorber 66 to remove H$_2$. A hydrogen-lean fraction is used as fuel," while the rest is further processed for ammonia production. ('846 patent, Col. 4, lines 38-57.)

A result of a continuation-in-part filing from the patent application which resulted in the '846 patent, U.S. Pat. No. 6,976,362 B2 by Sheppard et al. ("the '362 patent"), incorporated herein in its entirety by reference for all purposes not contrary to this disclosure, also describes an alternative to the conventional process described above with respect to FIGS. 1 and 2 of the present disclosure. The '362 patent describes a Fischer Tropsch plant "with greatly reduced emissions of carbon dioxide to the atmosphere is made up of a syngas generator unit, an air separation unit, a Fischer-Tropsch unit, a CO$_2$ removal unit, and a combined cycle electricity generation unit. Each of Fischer-Tropsch liquids, carbon dioxide, and electrical power can be recoverable under proper economic conditions. Electrical power is recoverable by the use of a gas turbine fueled by predominantly hydrogen and a steam turbine powered by steam generated by cooling exhaust gases from the gas turbine. Sequestration of CO$_2$ and fueling the gas turbine with hydrogen reduces the amount of greenhouse gases emitted to the atmosphere." ('362 patent, Abstract).

If a system to recycle unreacted syngas from the FT tail gas is used, such as that disclosed by the '846 patent and the '362 patent, a purge stream is required to remove inerts that build over time from the system. The unreacted syngas purge stream comprises an FT tail gas that contains valuable carbon in the form of carbon monoxide (CO). Typically, the unreacted syngas purge stream is mixed in with the plant fuel gas and burned, and the potentially valuable carbon is emitted as carbon dioxide (CO$_2$) in the flue gas.

Accordingly, there are needs in the art for novel systems and methods for capturing value from FT tail gas purge streams.

SUMMARY

The disclosure includes one or more embodiments of a method of producing Fischer-Tropsch ("FT") hydrocarbons via FT synthesis in an FT reactor having an FT synthesis catalyst, which includes the steps of producing a syngas comprising hydrogen and carbon monoxide in a syngas preparation unit using a carbonaceous feed, producing a liquid FT hydrocarbon stream, an FT tail gas stream and an FT water stream using the syngas gas as a feed in the FT reactor under FT operating conditions, removing an FT tail gas purge stream from the FT tail gas stream, leaving a remainder FT tail gas stream, treating the FT tail gas purge stream with steam in a water gas shift ("WGS") reactor, having a WGS catalyst, to produce carbon dioxide and hydrogen, which form a shifted FT purge stream, and treating the shifted FT purge stream in a carbon dioxide removal unit, which removes carbon dioxide from the shifted FT purge stream, producing a carbon dioxide stream and a treated purge stream. One or more embodiments include the carbon dioxide stream being recycled upstream of an input of the syngas preparation unit or immediately upstream of an input of the FT reactor or being divided for recycling to both the input of the syngas preparation unit or to the input of the FT reactor. The carbon dioxide stream may be recycled anywhere upstream of the FT reactor, depending on the particulars of the FT process utilized.

The disclosure includes one or more embodiments of a method of enhancing a Fischer-Tropsch ("FT") purge stream, which includes the steps of removing an FT tail gas purge stream from an FT tail gas produced by an FT reactor, treating the FT tail gas purge stream with steam in a water gas shift ("WGS") reactor, having a WGS catalyst, to produce a shifted FT purge stream including carbon dioxide and hydrogen, and removing at least a portion of the carbon dioxide from the shifted FT purge stream to produce a carbon dioxide stream and a treated purge stream. The carbon dioxide stream may be recycled to an input of the syngas preparation unit or to an input of the FT reactor. One or more embodiments include the carbon dioxide stream being recycled upstream of an input of the syngas preparation unit or immediately upstream of an input of the FT reactor or being divided for recycling to both the input of the syngas preparation unit or to the input of the FT reactor. The carbon dioxide stream may be recycled anywhere upstream of the FT reactor, depending on the particulars of the FT process utilized.

The disclosure includes one or more embodiments of a system for producing Fischer Tropsch ("FT") hydrocarbons. The system includes a syngas preparation unit for using a sweet natural gas and a steam as inputs to produce a flue gas and a syngas comprising hydrogen and carbon monoxide. The system also includes a syngas conditioning unit, an input of which is fluidly connected to a syngas output of the syngas preparation unit, configured to remove a process condensate stream from the syngas and produce a conditioned syngas. An FT reactor having an FT catalyst, is fluidly connected to the output of the syngas conditioning unit, and is configured to use the conditioned syngas as an input to make an FT tail gas, an FT water, and FT liquid hydrocarbons. An FT tail gas flowline transports at least a portion of the FT tail gas from the FT reactor to the syngas preparation unit for use as a feed. A diverting line is positioned to remove an FT tail gas purge stream, comprising a portion of the FT tail gas, from the FT tail gas in the FT tail gas flowline. The system further includes a water gas shift ("WGS") reactor fluidly connected to the diverting line to receive the FT tail gas purge stream. The WGS reactor has a water gas shift catalyst positioned therein, such that carbon monoxide and water in the FT purge stream exposed to the water gas shift catalyst and steam under WGS conditions is converted at least in part to carbon dioxide and hydrogen to form a shifted FT purge stream. The system also includes a carbon dioxide removal unit, fluidly connected to an output of the WGS reactor, configured to remove at least a portion of the carbon dioxide from a stream comprising the shifted FT purge stream to form a carbon dioxide stream and a treated purge stream.

The disclosure includes one or more embodiments of a system for utilizing a Fischer-Tropsch ("FT") tail gas purge stream, which includes a water gas shift ("WGS") reactor, having a WGS catalyst, a WGS input for accepting the FT tail gas purge stream and steam, and a WGS output for a shifted FT purge stream. The system also includes a carbon dioxide removal unit, having an input and an output, for removing carbon dioxide from the shifted FT purge stream to form a carbon dioxide stream and a treated purge steam, and a flowline fluidly connecting the WGS output with the input of the carbon dioxide removal unit. One or more embodiments include the carbon dioxide stream being recycled to an input of a syngas preparation unit or to an input of an FT reactor or to divided to be recycled to both.

The disclosure includes one or more embodiments of an apparatus for utilizing a FT purge stream including a water gas shift ("WGS") reactor, having a WGS catalyst, and a WGS input for accepting an FT purge gas, a second WGS input for accepting steam, a WGS output for a shifted FT purge stream and a process condensate outlet.

These and other embodiments, features and advantages will be apparent in the following detailed description and drawings.

BRIEF DESCRIPTION OF THE DRAWINGS

For a more detailed description of the present invention, reference will now be made to the accompanying drawings, wherein.

NOTATION AND NOMENCLATURE

Figure 1:
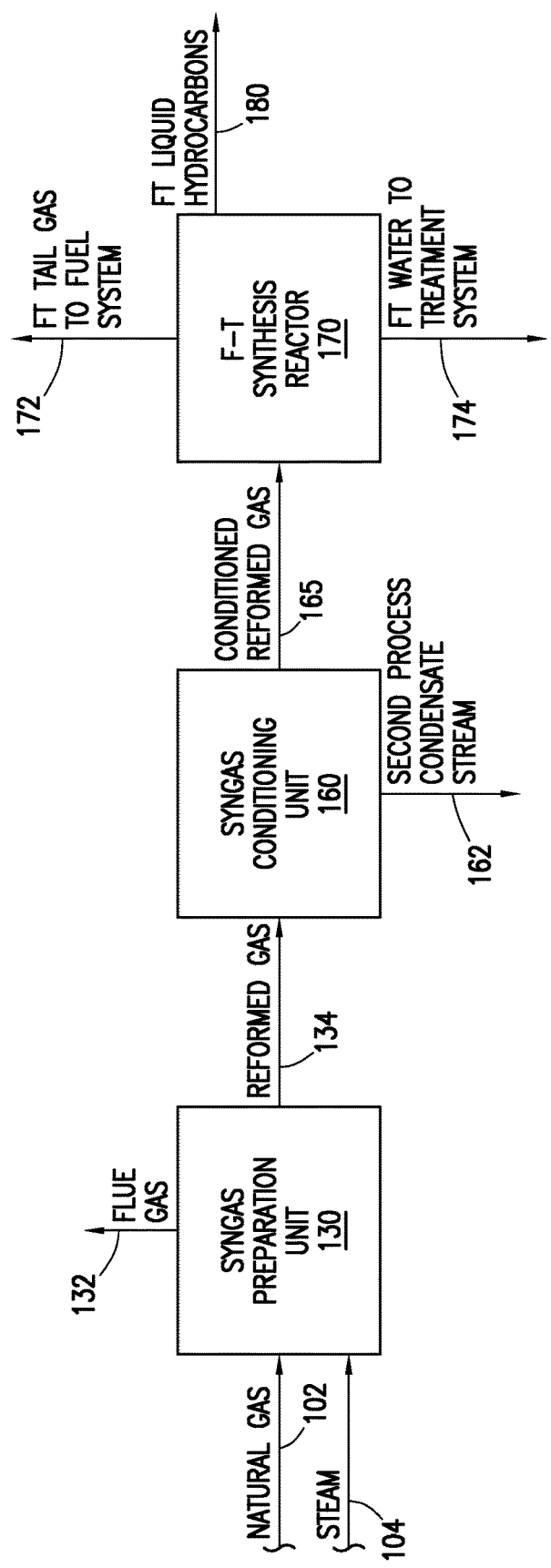
FIG. 1 depicts a simplified block diagram for a conventional Fischer Tropsch system, including a steam methane configuration.
Figure 2:
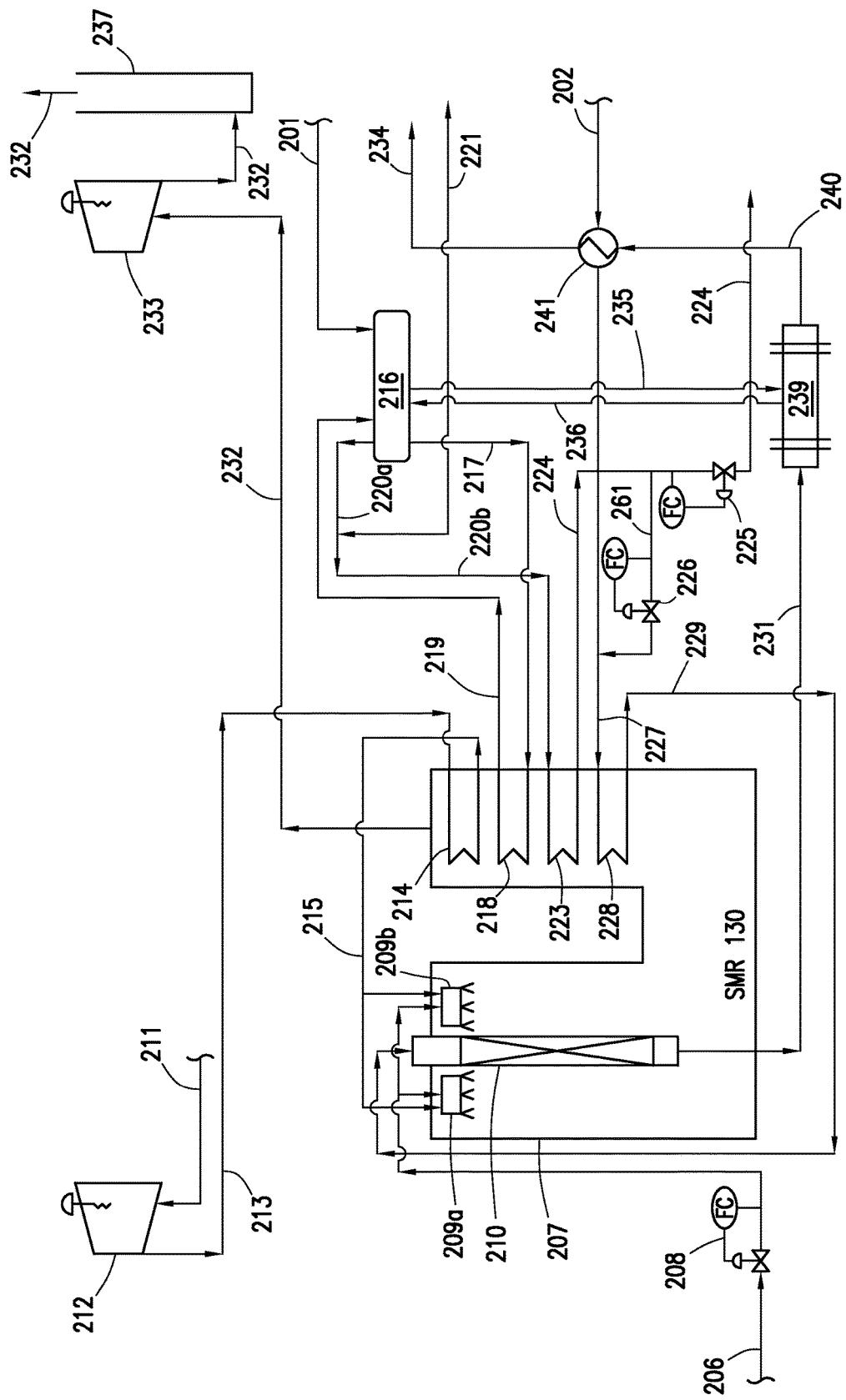
FIG. 2 depicts a more detailed view of the conventional SMR 130 of FIG. 1.

As used herein, the term "carbonaceous feedstock(s)" means carbon-containing energy source(s), such as coal, natural gas, biomass, or carbonaceous waste streams (such as municipal solid waste) that can be converted into syngas. Some carbon energy sources must be pre-treated and/or gasified before use as a feedstock to a syngas preparation unit.

As used herein, the abbreviation "FT" and/or "F-T" stand for Fischer-Tropsch (which may be written "Fischer Tropsch").

As used herein, the term "FT tail gas" means gas produced from an FT reactor. The FT tail gas may typically contain unreacted hydrogen and carbon monoxide, as well as carbon dioxide, some light hydrocarbons, and other light reaction byproducts.

As used herein, the terms "FT purge stream" or "FT tail gas purge stream" have an identical meaning and mean excess FT tail gas removed from the primary FT tail gas stream. The FT purge stream typically has the same composition as the FT tail gas.

As used herein, the term "FT water" means water produced by an FT reaction. The water will typically include dissolved oxygenated species, such as alcohols, and light hydrocarbons.

As used herein, with respect to an FT plant, (1) the abbreviation "GTL" stands for gas-to-liquids; (2) the abbreviation "CTL" stands for coal-to-liquids; (3) the abbreviation "BTL" stands for biomass-to-liquids; and (4) the abbreviation "WTL" stands for waste-to-liquids. The first letter of each abbreviation stands for the respective carbonaceous feedstock used to create syngas that is used as a feed to an FT reactor to make liquid FT products. Thus, for example, GTL plants use natural gas to make the syngas used as a feed for the FT reactor.

As used herein, the phrase "a high-temperature Fischer-Tropsch (or 'HTFT') reactor" means an FT reactor that is typically operated at temperatures of 330° C.-350° C., which typically employs an iron-based catalyst. This process has been put to use extensively by Sasol in their Coal-to-Liquid (CTL) plants. As used herein, the phrase "a low-temperature Fischer-Tropsch (or 'LTFT') reactor" means an FT reactor that is operated at lower temperatures, generally in a range between 170° C.-235° C., which typically employs a cobalt-based catalyst. As used herein, the phrase "a low-temperature, high-pressure Fischer-Tropsch (or 'LTHP FT') reactor" means an LTFT reactor that is operated at high pressures, such as between 300 psig and 600 psig.

As used herein, the term "liquid FT hydrocarbon products" means liquid hydrocarbons produced by an FT reactor.

As used herein, the terms "reformed gas" or "synthesis gas" or "syngas" means the effluent from a syngas preparation unit, such as (without limitation) a steam methane reformer, autothermal reformer, hybrid reformer, or partial oxidation reformer. Steam methane reformers do not use oxygen as part of the process; autothermal reformers do. Both use reformer catalysts. Hybrid reformers are a combination of steam methane reforming, as a first step, and an autothermal reforming with oxidation as a second step. Partial oxidation reformers are similar to autothermal reformers, but do not include the use of a reformer catalyst.

As used herein, the term "sweet natural gas" means natural gas from which any excess sulfur or sulfur compounds such as, for example, $H_2S$ has been previously removed.

As used herein, the term "to superheat" a fluid means to heat the fluid above its steam dew point (or saturation point). Specific preferred temperature ranges are noted, although other temperatures typically may be used.

As used herein, the term "tubular reactor" refers to Fischer-Tropsch reactors containing one or more tubes containing FT catalyst, wherein the inner diameter or average width of the one or more tubes is typically greater than about 0.5".

Use of the term "tubular" is not meant to be limiting to a specific cross sectional shape. For example, tubes may have a cross-sectional shape that is not circular. Accordingly, the tubes of a tubular reactor may, in one or more embodiments, have a circular, oval, rectangular, and/or other cross sectional shape(s).

As used herein and as mentioned above, the abbreviation "WGS" stands for water gas shift and the abbreviation "WGSR" stands for water-gas-shift reaction.

DETAILED DESCRIPTION

Figure 3:
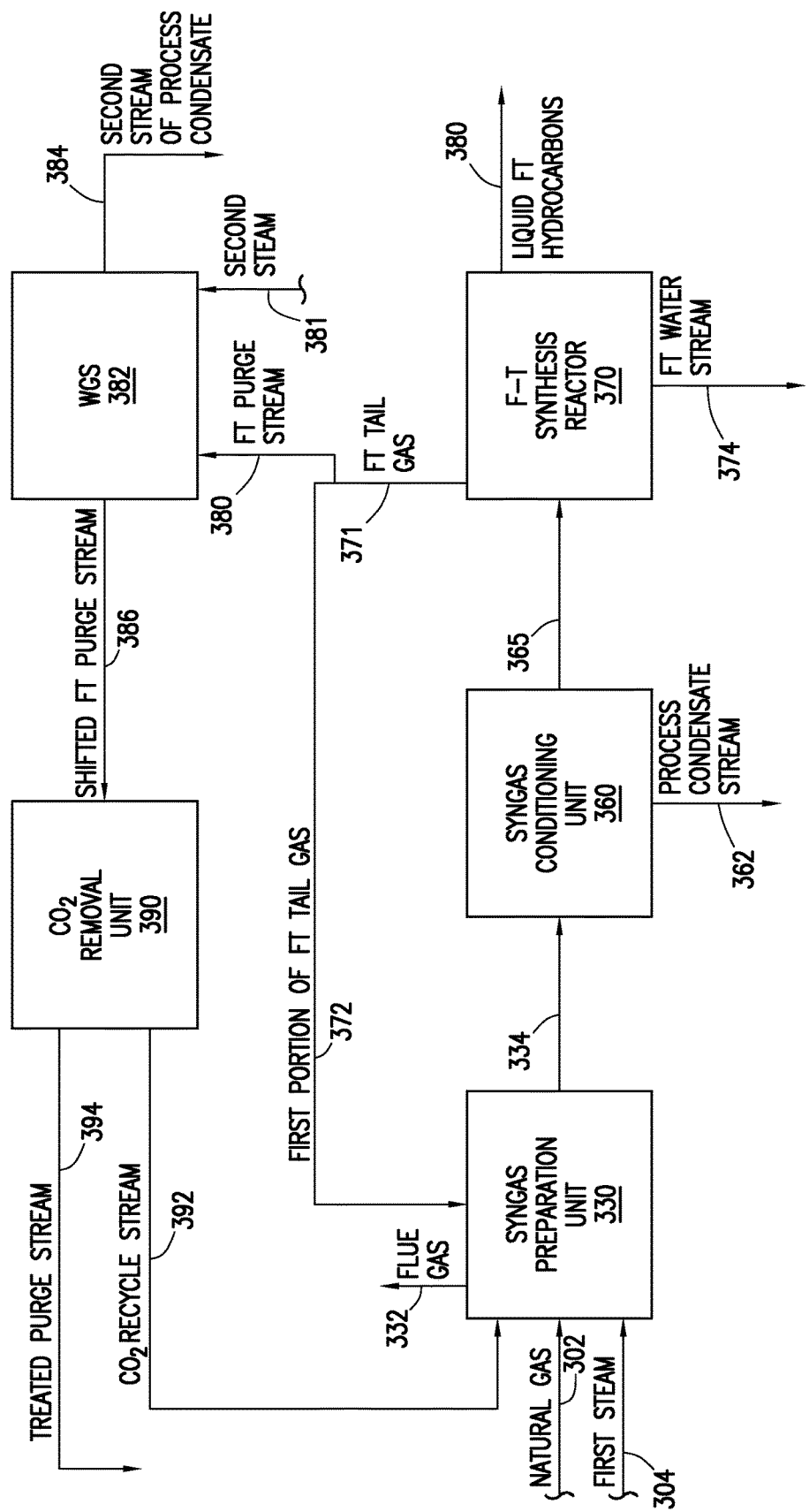
FIG. 3 is a block diagram of a Fisher Tropsch system including utilizing an FT tail gas purge stream, in accordance with one or more embodiments of the present disclosure.

FIG. 3 depicts a simplified flow diagram for a Fischer Tropsch system in accordance with one or more embodiments of the present disclosure. Natural gas 302 and a first steam stream 304 enter a syngas preparation unit 330 as feeds. The natural gas 302 entering the syngas preparation unit 330 is preferably sweet natural gas, from which any excess sulfur or sulfur compounds such as $H_2S$ has been previously removed. In alternate embodiments, one or more other carbonaceous feedstocks may be used instead of or in addition to the natural gas 302. The syngas preparation unit 330 may comprise, for example, a steam methane reformer, an autothermal reformer, a hybrid reformer, or a partial oxidation reformer. As is known in the art, different types of syngas preparation units have different requirements and may be configured differently. Fox example, an autothermal syngas preparation unit would require an oxygen source, which is not depicted on FIG. 3. A flue gas 332 and a reformed gas ("syngas") 334 exit the syngas preparation unit 330 via a first flowline and a second flowline respectively. (Flowlines in FIG. 3 are not separately numbered or depicted, except with the fluids they carry.) The reformed gas 334 passes to a syngas conditioning unit 360, whereby a process condensate stream 362 is collected and the hydrogen and carbon monoxide ratios are adjusted to pre-determined levels, if needed. Conditioned reformed syngas 365 is sent via a third flowline to an FT synthesis reactor 370 (or "FT reactor") as a feed for use in creating FT hydrocarbons. The FT reactor 370 includes an FT catalyst and operates under FT conditions, which may vary somewhat depending on the type of FT reactor used. The FT reactor produces liquid FT hydrocarbons 380, with byproducts including an FT tail gas 371, and an FT water stream 374, and.

In one or more embodiments, the FT reactor 370 comprises a fixed bed Fischer-Tropsch reactor. In one or more embodiments, the FT reactor 370 comprises a tubular Fischer-Tropsch reactor. In one or more embodiments, the FT reactor 370 comprises a fluidized bed Fischer-Tropsch reactor. In one or more embodiments, the FT reactor 370 comprises a slurry bed Fischer-Tropsch reactor, such as, but not limited to, a slurry bubble column Fischer-Tropsch reactor. In one or more embodiments, the FT reactor 370 comprises an FT reactor of any type.

The disclosed FT reactor 370 of FIG. 1 and system and method used therewith may employ one or more of a variety of FT catalytic metals, such as Group 8-10 metals, including, but not limited to, iron, nickel, ruthenium, and/or cobalt. As discussed further herein below, in one or more embodiments of the present disclosure, cobalt-based catalysts may be employed. As known in the art, a cobalt-based FT catalyst may comprise cobalt impregnated into or onto any convenient catalyst carrier or support material, including, but not limited to, alumina ($Al_2O_3$), titania ($TiO_2$), and silica ($SiO_2$). Exotic carriers and promoters, such as platinum (Pt), palladium (Pd), rhenium (Re), and ruthenium (Ru) may also be employed. Other suitable catalyst carrier(s) and promoter(s) are known in the art and may be incorporated. The FT catalyst carrier may be in any convenient shape (e.g., spheres, pellets, trilobes, etc.).

Referring again to FIG. 3, in one or more embodiments of the present disclosure, an FT purge stream 380 is removed from the FT tail gas 371. This may be performed in different ways. For example, a pressure regulator, a pressure-activated control value or a diverting line could be used. The FT purge stream 380 is sent to a water gas shift (WGS) reactor 382. The WGS reactor may be a low temperature WGS reactor, a medium temperature WGS reactor, or a high temperature WGS reactor. In one or more embodiments, two or more WGS reactors may be used in series, with or without intermediate cooling. The WGS reactor may use a WGS catalyst (not separately depicted in FIG. 3), such as a copper-based low temperature shift catalyst, such as Shiftmax® 230 low temperature shift catalyst offered by Clariant. For a high temperature WGS reactor, an iron-based high temperature shift catalyst might be used. A second steam stream 381 is added to the WGS reactor 382. By exposing the FT purge stream 380 to the second steam stream 381 and the WGS catalyst in the WGS reactor 382, carbon monoxide and water of the FT purge stream 380 are converted into carbon dioxide and hydrogen, forming a shifted FT purge stream 386. The WGS reactor 382 would likely not consume all of the water from the added second steam stream 381. Unused water from the second steam stream 381 not consumed by the WGS reactor 382 may be condensed to form a second stream of process condensate 384.

Continuing to refer to FIG. 3, the shifted FT purge stream 386 is sent to a carbon dioxide removal unit 390, which removes carbon dioxide from the shifted FT purge stream 386. The carbon dioxide removal unit may be any appropriate carbon dioxide removal unit, including but not limited to an amine unit or a carbon dioxide removal membrane.

The removed carbon dioxide forms a carbon dioxide recycle stream 392, which may be sent as an additional input to the syngas preparation unit 330, as depicted in FIG. 3. Alternatively, the removed carbon dioxide may be sequestered or otherwise properly disposed of or may be recycled to the FT reactor. In embodiments wherein the syngas preparation unit comprises a steam methane reformer, additional $CO_2$ in the feed to the steam methane reformer is believed to suppress the formation in the steam methane reformer of undesirable excess hydrogen by facilitating the reverse shift reaction:

$$CO_2 + H_2 \iff CO + H_2O. \tag{4}$$

Accordingly, provision of additional $CO_2$ to a steam methane reformer, for example through recycling of $CO_2$, may be beneficial.

The carbon dioxide removal unit 390 also produces a treated purge stream 394. The treated purge stream 394 may contain hydrogen and may be used for fuel for the steam methane reformer 330 or for other plant purposes, such as hydrotreating FT wax.

In one or more embodiments of the present disclosure, as depicted in FIG. 3, at least a first portion 372 of the FT tail gas, from which the FT purge stream 380 has been removed, is sent via a fourth flowline to the syngas preparation unit 330, where the first portion of the FT tail gas is used as an additional feed. The FT water 374 may be treated for disposal or may be recycled. Such recycling of the FT tail gas and the FT water are described in the previously mentioned, U.S. Provisional Application No. 62/005,102.

Figure 4:
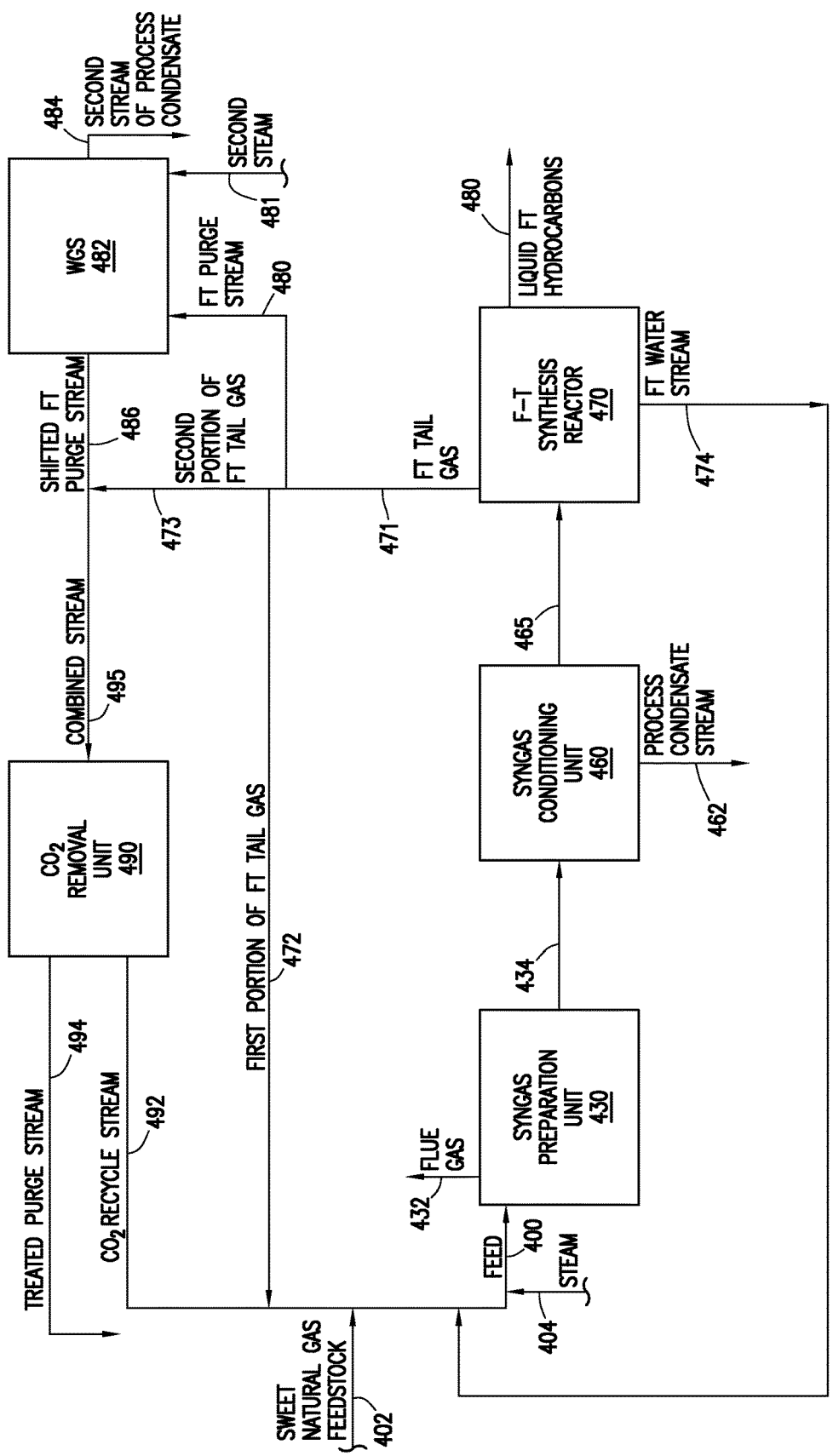
FIG. 4 is a block diagram of a Fisher Tropsch system, wherein a carbon dioxide recycle stream is combined with a portion of an FT tail gas stream before being recycled to a front end of a syngas preparation unit, in accordance with one or more embodiments of the present disclosure.

FIG. 4 depicts a block diagram of one or more embodiments of the present disclosure. A feed 400, including a natural gas feedstock 402 and a first steam stream 404, enters a syngas preparation unit 430. The syngas preparation unit 430 may comprise, for example, a steam methane reformer, an autothermal reformer, a hybrid reformer, or a partial oxidation reformer. The feed 400 is further described below. A flue gas 432 and a syngas 434 exit the syngas preparation unit 330 via a first flowline and a second flowline respectively. (Flowlines in FIG. 4 are not numbered separately from the fluids carried therein.) The reformed gas 434 passes to a syngas conditioning unit 460, whereby a stream of clean process condensate 462 is collected and the hydrogen and carbon monoxide ratios may be adjusted to pre-determined levels, if needed. Conditioned syngas 465 is sent from syngas conditioning unit 460 via a third flowline to an FT synthesis reactor 470 as a feed for use in creating FT hydrocarbons. The FT synthesis reactor 470 includes an FT catalyst (not separately depicted) and operates under FT operating conditions. Product and by-products of the FT reactor 470 include liquid FT hydrocarbons 480, an FT tail gas 471, and an FT water stream 474.

Referring again to FIG. 4, an FT purge stream 480 is removed from the FT tail gas 471. This may be performed in different ways. For example, a pressure regulator, a pressure-activated control value or a diverting line could be used. The FT purge stream 480 is sent to a water gas shift (WGS) reactor 482. The WGS reactor 482 may be a low temperature WGS reactor, a medium temperature WGS reactor, or a high temperature WGS reactor. In one or more embodiments, two or more WGS reactors 482 may be used in series, with or without intermediate cooling. The WGS reactor 482 may use a WGS catalyst (not separately depicted in FIG. 4), such as a copper-based low temperature shift catalyst, such as Shiftmax® 230 low temperature shift catalyst offered by Clariant. For a high temperature WGS reactor, an iron-based high temperature shift catalyst might be used. A second steam 481 is added to the WGS reactor 482. By exposing the FT purge stream 480 to the second steam 481 and the WGS catalyst in the WGS reactor 482, carbon monoxide and water in the FT purge stream 480 are converted into carbon dioxide and hydrogen, forming a shifted FT purge stream 486. The WGS reactor 482 would likely not consume all of the water from the added second steam 481. Unused water from the second steam 481 not consumed by the WGS reactor 482 may be condensed to form a third stream of process condensate 484.

As in FIG. 3, a first portion 472 of the FT tail gas is recycled via a fourth flowline to become part of the feed 400 to the syngas preparation unit 430. By contrast with the embodiment(s) depicted in FIG. 3, in FIG. 4, a second portion 473 of the FT tail gas is sent via a sixth flowline to join with the shifted FT purge stream 486 to form a combined stream 495. The combined stream 495 is sent to a carbon dioxide removal unit 490, where carbon dioxide is removed from the combined stream 495, resulting in a $CO_2$ recycle stream 492 and a treated purge stream 494, carried by seventh and eighth flowlines respectively. The carbon dioxide removal unit 490 may be any appropriate carbon dioxide removal unit, including but not limited to an amine unit or a carbon dioxide removal membrane. The $CO_2$ recycle stream 492 is added to the first portion 472 of the FT tail gas upstream of the syngas preparation unit 430. (Alternatively, the removed carbon dioxide may be sequestered or otherwise disposed of or may be recycled to the FT reactor.) In FIG. 4, the sweet natural gas feedstock 402 is also combined with the $CO_2$ recycle stream 492 and the first portion 472 of the FT tail gas upstream of the syngas preparation unit 430. In alternate embodiments, one or more other carbonaceous feedstocks may be used instead of or in addition to the sweet natural gas 402. As in FIG. 3, in FIG. 4, the carbon dioxide removal unit 490 also produces a treated purge stream 494. The treated purge stream 494 may contain hydrogen and may be used for fuel for the steam methane reformer 430 or for other plant purposes, such as for hydrotreating FT wax.

The FT water stream 474 may be treated for disposal or may be recycled into the feed 400 for the syngas preparation unit 430. Such recycling of the FT tail gas and the FT water stream are described in the previously mentioned, U.S. Provisional Application No. 62/005,102. In FIG. 4, the FT water stream 474 is injected into the combination of the sweet natural gas feedstock 402, the $CO_2$ recycle stream 492, and the first portion 472 of the FT tail gas upstream of the syngas preparation unit 430. Injecting the FT water stream 474 into the combination of the sweet natural gas 402, the $CO_2$ recycle stream 492 and the first portion 472 of the FT tail gas upstream of the syngas preparation unit 430 may be advantageous, as the combination provides a greater volume of gas into which the FT water is injected than there would be if the FT water 474 were injected into the first portion 472 of the FT tail gas alone.

Figure 5:
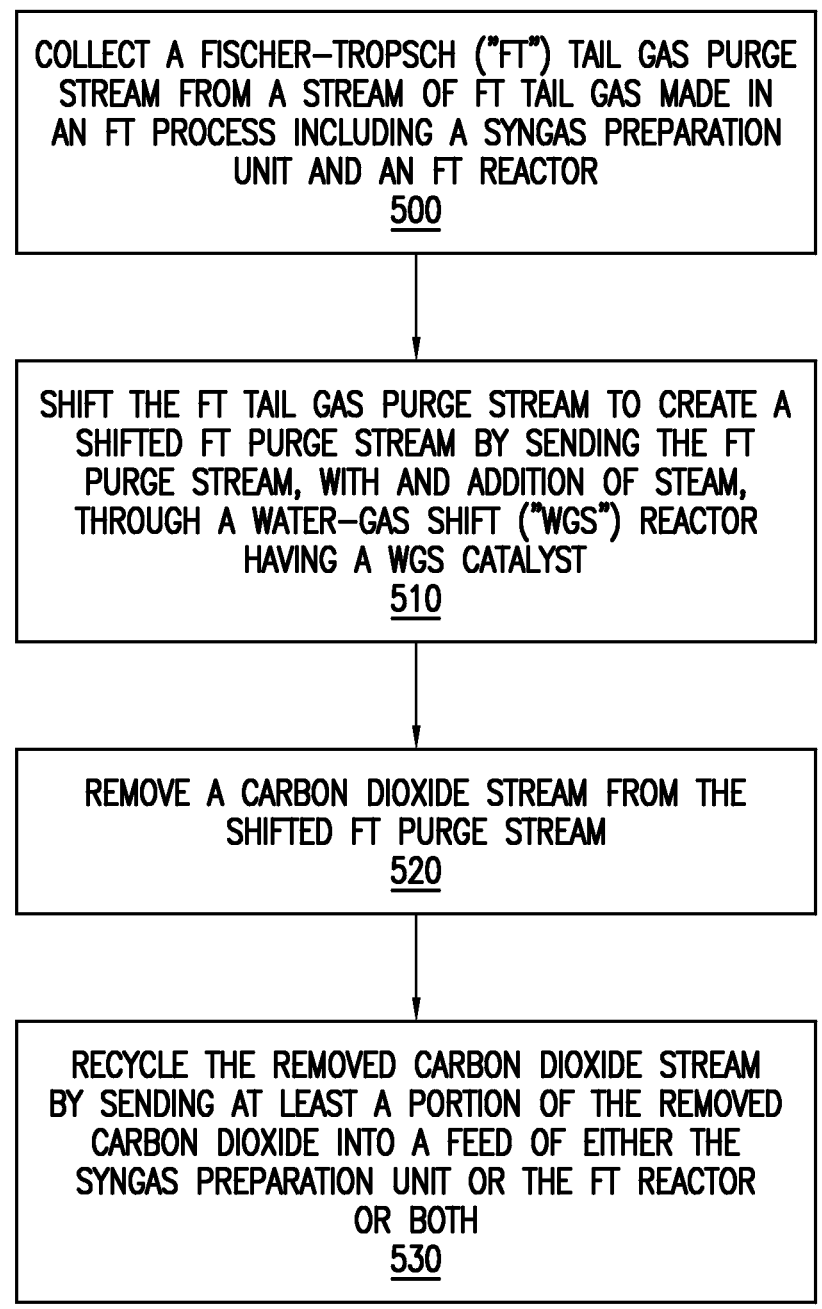
FIG. 5 is a flowchart for a method of utilizing an FT tail gas purge stream in accordance with one or more embodiments of the present disclosure.

FIG. 5 is flowchart for utilizing an FT tail gas purge stream in accordance with one or more embodiments of the present disclosure. Step 500 is to collect an FT tail gas purge stream from a stream of FT tail gas made in an FT process including a syngas preparation unit and an FT reactor. The FT tail gas purge stream is shifted 510 to create a shifted FT purge stream by sending the FT tail gas purge stream, with an addition of steam, through a water-gas shift ("WGS") reactor having a WGS catalyst. In step 520, a carbon dioxide stream is removed from the shifted FT purge stream. The carbon dioxide removal may be performed, for example, by using an amine unit. At least a portion of the removed carbon dioxide stream is recycled in step 530, by being sent as an input (or as a part of a feed which is an input) to either the syngas preparation unit or the FT reactor or both. Preferably, all of the removed carbon dioxide is recycled, but that may depend on the specifics of the particular FT process being used. The treated purge stream may contain hydrogen and may be used for fuel for the steam methane reformer or for other plant purposes, such as hydrotreating FT wax.

While some preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations. The use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

Accordingly, the scope of protection is not limited by the description set out above but is only limited by the claims that follow, that scope including all equivalents of the subject matter of the claims. Each and every claim is incorporated into the specification as an embodiment of the present invention. Thus, the claims are a further description and are an addition to the preferred embodiments of the present invention. The inclusion or discussion of a reference is not an admission that it is prior art to the present invention, especially any reference that may have a publication date after the priority date of this application. The disclosures of all patents, patent applications, and publications cited herein are hereby incorporated by reference, to the extent that they provide background knowledge; or exemplary, procedural or other details supplementary to those set forth herein.

What is claimed is:

1. A method of producing Fischer-Tropsch ("FT") hydrocarbons via FT synthesis in an FT reactor having an FT synthesis catalyst, the method comprising:
   a. producing a syngas comprising hydrogen and carbon monoxide in a syngas preparation unit, comprising a stream methane reformer, using a carbonaceous feed;
   b. producing a liquid FT hydrocarbon stream, an FT tail gas stream and an FT water stream using the syngas gas as a feed in the FT reactor under FT operating conditions;
   c. removing an FT tail gas purge stream from the FT tail gas stream, leaving a remainder FT tail gas stream;
   d. treating the FT tail gas purge stream with steam in a water gas shift ("WGS") reactor, having a WGS catalyst, to produce carbon dioxide and hydrogen, which form a shifted FT purge stream; and e. treating the shifted FT purge stream in a carbon dioxide removal unit, which removes carbon dioxide from the shifted FT purge stream, producing a carbon dioxide stream and a treated purge stream; and f. further comprising recycling the carbon dioxide stream as an input to the steam methane reformer.

2. The method of claim 1, wherein the WGS reactor comprises a low temperature water gas shift reactor.

3. The method of claim 1, wherein the WGS reactor comprises a medium temperature water gas shift reactor.

4. The method of claim 1, wherein the WGS reactor comprises a high temperature water gas shift reactor.

5. The method of claim 1, wherein two or more WGS reactors are used in series to treat the FT tail gas purge stream.

6. The method of claim 1, further comprising recycling the remainder FT tail gas stream as an input to the syngas preparation unit.

7. The method of claim 1, further comprising using the treated purge stream as fuel for the syngas preparation unit.

8. The method of claim 1, further comprising using the treated purge stream to sweeten natural gas.

9. The method of claim 1, further comprising using the treated purge stream to hydrotreat FT wax.

10. The method of claim 1, wherein the carbon dioxide removal unit is an amine unit.

11. The method of claim 1, wherein the carbon dioxide removal unit is carbon dioxide removal membrane.

12. A method of enhancing a Fischer-Tropsch ("FT") purge stream, comprising:

a. removing an FT tail gas purge stream from an FT tail gas produced by an FT reactor, leaving a remainder FT tail gas;

b. treating the FT tail gas purge stream with steam in a water gas shift ("WGS") reactor, having a WGS catalyst, to produce a shifted FT purge stream comprising carbon dioxide and hydrogen;

c. removing at least a portion of the carbon dioxide from the shifted FT purge stream, thereby producing a carbon dioxide stream and a treated purge stream; and d. further comprising using the carbon dioxide stream as an input to a steam methane reformer acting as a syngas preparation unit.

13. The method of claim 12, wherein the water gas shift reactor comprises a low temperature water gas shift reactor.

14. The method of claim 12, wherein the water gas shift reactor comprises a medium temperature water gas shift reactor.

15. The method of claim 12, wherein the water gas shift reactor comprises a high temperature water gas shift reactor.

16. The method of claim 12, wherein two or more WGS reactors are used in series to treat the FT tail gas purge stream.

17. The method of claim 12, further comprising recycling the remainder FT tail gas as an input to a front end of the steam methane reformer.

18. The method of claim 12, further comprising using the treated purge stream as a fuel for the syngas preparation unit.

19. The method of claim 12, wherein the step of removing at least a portion of the carbon dioxide from the shifted FT purge stream is performed using a carbon dioxide removal membrane.

20. The method of claim 12, wherein the step of removing at least a portion of the carbon dioxide from the shifted FT purge stream is performed using an amine unit.

21. The method of claim 1, further comprising removing a second portion of the FT tail gas from the FT tail gas and adding the second portion of the FT tail gas to the shifted purge stream to form a combined stream, prior to treatment of the combined stream in the carbon dioxide removal unit.

22. The method of claim 12, further comprising removing a second portion of the FT tail gas from the FT tail gas and adding the second portion of the FT tail gas to the shifted purge stream to form a combined stream, prior to treatment of the combined stream in the carbon dioxide removal unit.

* * * * *